United States Patent [19]
De Nanteuil et al.

[11] Patent Number: 6,040,327
[45] Date of Patent: Mar. 21, 2000

[54] BENZIMIDAZOLE, BENZOXAZOLE AND BENZOTHIAZOLE COMPOUNDS

[75] Inventors: Guillaume De Nanteuil, Suresnes; Bernard Portevin, Elancourt; Jacqueline Bonnet, Paris; Armel Fradin, Neuilly sur Seine, all of France

[73] Assignee: Adir Et Compagnie, Courbevoie, France

[21] Appl. No.: 09/120,487

[22] Filed: Jul. 22, 1998

[30] Foreign Application Priority Data

Jul. 30, 1997 [FR] France .................................. 97.09710

[51] Int. Cl.[7] ........................ A61K 31/415; C07D 403/04
[52] U.S. Cl. ........................ 514/394; 546/118; 546/273.4; 548/159; 548/181; 548/235; 548/266.4; 548/305.4; 548/306.1; 514/303; 514/338; 514/365; 514/367; 514/374; 514/383
[58] Field of Search .............................. 548/306.1, 305.4, 548/266.4, 159, 181, 235; 514/394, 383, 367, 365, 303, 338, 374; 546/118, 273.4

[56] References Cited

U.S. PATENT DOCUMENTS 5,552,426  9/1996  Lunn et al. .............................. 514/394

FOREIGN PATENT DOCUMENTS 1450560  8/1966  France .
3819823  12/1989  Germany .
2-306916  12/1990  Japan .
95/19772  7/1995  WIPO .

OTHER PUBLICATIONS

Chimetron, CA 66:76010, 1967.
Dykstra, CA 123:218384, 1995.

*Primary Examiner*—Laura L. Stockton
*Attorney, Agent, or Firm*—The Firm of Gordon W. Hueschen

[57] ABSTRACT

A compound of formula (I):

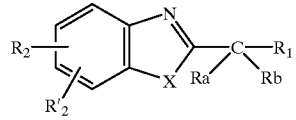

(I)

wherein:

$R_1$ represents halogen or a different group as defined in the description,

Ra and Rb, which mnay be identical or different, represent hydrogen, alkyl, or hydroxy, X represents oxygen or sulphur or NR, R being H or alkyl, $R_2$ represents optionally-substituted aryl, $R'_2$ represents hydrogen or optionally-substituted aryl, its isomers and addition salts thereof with a pharmaceutically-acceptable acid or base, and medicinal products containing the same, are useful as inhibitors of interleukin 1β.

16 Claims, No Drawings

BENZIMIDAZOLE, BENZOXAZOLE AND BENZOTHIAZOLE COMPOUNDS

FIELD OF THE INVENTION

The present invention relates to new benzimidazole, benzoxazole and benzothiazole compounds. The compounds of the present invention are powerful inhibitors of interleukin 1β (IL1β) and of her formation.

BACKGROUND OF THE INVENTION

IL1β is produced by macrophages and has a wide variety of biological activities associated with inflammatory pathologies, such as rheumatoid arthritis or arthrosis.

IL1β stimulates those cells present in joints that produce and then express inducible cyclo-oxygenase (COX2), and inducible NO synthase, to provide prostaglandins and NO, which are important mediators of pain and inflammation. IL1β also activates the expression and production of proteases which are involved in degrading the extracellular matrix of chondrocytes and in suppressing the synthesis of the components of the cartilage matrix.

Moreover, IL1β is involved in activating endothelial cells which then express different adhesion factors, and in inducing other pro-inflammatory cytokines, such as TNF or the chemokines (IL6). Finally, IL1β plays a role in the regulation of bone resorption and in lymphocyte differentiation and proliferation.

An IL1β inhibitor can therefore be expected to be active against inflammatory phenomena and to modify favourably the development of pathologies such as rheumatoid arthritis or arthrosis.

DETAILED DESCRIPTION OF THE INVENTION

More specifically, the present invention relates to compounds of formula (I):

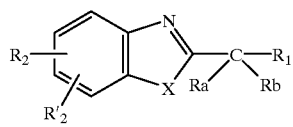

(I)

wherein:
- $R_1$ represents a halogen atom, a hydroxy group, a linear or branched ($C_1$–$C_6$)alkoxy group (optionally substituted by an aryl group), a trihalomethyl group, an arylmethyl group, a cyano group, a sulpho group, an amino group (optionally substituted by one or more, identical or different, linear or branched ($C_1$–$C_6$)alkyl, optionally substituted aryl, acyl, arylsulphonyl and/or alkylsulphonyl groups), a mercapto group, a linear or branched ($C_1$–$C_6$)alkylthio group, a linear or branched ($C_1$–$C_6$)triallylarnmonium group, an aryloxy group, an arylthio group, an arylaminocarbonyl group, an arylcarbonylamino group, an arylsulphonylarnino group, an arylaminosulphonyl group, an arylureido group, an arylthioureido group, an arylsulphonyl group, an arylsulphonyloxy group, a ($C_3$–$C_7$)cycloalkyloxy group, a ($C_3$–$C_7$)cycloalkylthio group, a ($C_6$–$C_8$) bicycloalkyloxy group (optionally substituted by an aryl group) or a ($C_6$–$C_8$)bicycloalkythio group (optionally substituted by an aryl group), it being understood that each aryl group may be optionally substituted,
- Ra and Rb, which may be identical or different, represent a hydrogen atom, a hydroxy group or a linear or branched ($C_1$–$C_6$)alkyl group (optionally substituted by an aryl group),
- X represents an oxygen or sulphur atom or a group NR (wherein R represents a hydrogen atom or a linear or branched ($C_1$–$C_6$)alkyl group), triazolyl or tetrazolyl group, each of those groups being optionally substituted by one or more, identical or different, halogen atoms, linear or branched ($C_1$–$C_6$)alkyl, linear or branched ($C_1$–$C_6$)trihaloalkyl, linear or branched ($C_1$–$C_6$)alkoxy, nitro, cyano, carboxy, linear or branched ($C_1$–$C_6$)alkoxycarbonyl, hydroxy, amino (optionally substituted by one or more, identical or different, linear or branched ($C_1$–$C_6$)alkyl, acyl, alkylsulphonyl and/or arylsulfonyl groups), optionally substituted phenyl and/or optionally substituted bicycloalkyl groups,
- $R'_2$ represents a hydrogen atom or an optionally substituted aryl group, their isomers and addition salts thereof with a pharmaceutically acceptable acid or base.

The term "aryl group" is to be understood as meaning a mono- or bi-cyclic aromatic group optionally containing from 1 to 4 hetero atoms selected from nitrogen, sulphur and oxygen. The term "optionally substituted" applied to the aryl, phenyl and bicycloalkyl groups means a substitution of those groups by one or more, identical or different, halogen atoms, linear or branched ($C_1$–$C_6$)alkyl, linear or branched ($C_1$–$C_6$)trihaloalkyl, linear or branched ($C_1$–$C_6$)alkoxy (optionally substituted by a carboxy or alkoxycarbonyl group), hydroxy, nitro, cyano, amino (optionally substituted by one or more, identical or different. linear or branched ($C_1$–$C_6$)alkyl, acyl, alkylsulphonyl and/or arylsulphonyl groups), carboxy, linear or branched ($C_1$–$C_6$) alkoxycarbonyl, hydroxyaminocarbonyl, alkylsulphonylamino, arylsulfonylamino, alkylsulphonylaminocarbonyl, arylsulphonylaminocarbonyl, optionally substituted phenyl and/or optionally substituted bicycloalkyl groups.

Amongst the pharmaceutically acceptable acids there may be mentioned by way of nonlimiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Amongst the pharmaceutically acceptable bases there may be mentioned by way of nonlimiting example sodium hydroxide, potassium hydroxide, triethylamine, tert-butylamine, etc.

The preferred compounds of the invention are compounds of formula (I) wherein X represents a group NR as defined hereinabove.

The preferred $R_2$ group is an optionally substituted imidazolyl group.

The $R_1$ groups preferred according to the invention are optionally substituted aryloxy, optionally substituted arylthio or optionally substituted arylsulphonylamino groups.

The present invention relates also to a process for the preparation of compounds of formula (I). When the desired compounds of formula (I) are those wherein X=NR, the process is characterised in that there is used as starting material a compound of formula (I):

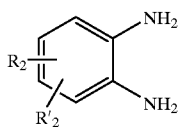

(II)

wherein $R_2$ and $R'_2$ are as defined for formula (I), which is reacted, in an acidic medium, with a compound of formula (III):

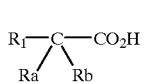

(III)

wherein $R_a$, $R_b$ and $R_1$ have the same meanings as for formula (I), to yield a compound of formula (I/a), which is a particular case of the compounds of formula (I):

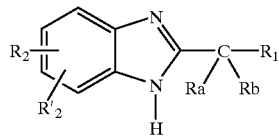

(I/a)

wherein $R_1$, $R_a$, $R_b$, $R_2$ and $R'_2$ are as defined for formula (I), which, when $R_1$ represents a hydroxy group, is optionally subjected to the action of thionyl chloride, to yield a compound of formula (I/b), which is a particular case of the compounds of formula (I):

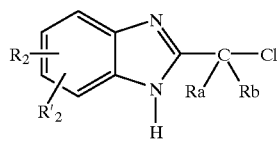

(I/b)

wherein $R_2$, $R'_2$, $R_a$ and $R_b$ have the same meanings as for formula (I), which may then be subjected to the conventional reactions that can be carried out on chlorinated compounds, to obtain the corresponding substitutions, which compound of formula (I/a) or (I/b):

the NH function of which may be optionally substituted by a linear or branched $(C_1–C_6)$alkyl group, may, if necessary, be purified in accordance with a conventional purification technique is separated, where appropriate, into its isomers in accordance with a conventional separation technique, and/or is converted, if desired, into addition salts thereof with a pharmaceutically acceptable acid or base.

When the desired compounds of formula (I) are those wherein X=X'=O or S, the process is characterised in that there is used as starting material a compound of formula (IV):

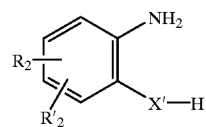

(IV)

wherein $R_2$ and $R'_2$ are as defined for formula (I) and X'=O or S, which is reacted, in an acidic medium, with a compound of formula (III):

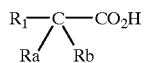

(III)

wherein $R_a$, $R_b$ and $R_1$ have the same meanings as for formula (I), to yield a compound of formula (I/c), which is a particular case of the compounds of formula (I):

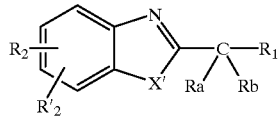

(I/c)

wherein $R_2$, $R'_2$, X', $R_a$, $R_b$ and R are as defined hereinabove, which, when $R_1$ represents a hydroxy group, is optionally subjected to the action of thionyl chloride, to yield a compound of formula (I/d), which is a particular case of the compounds of formula (I):

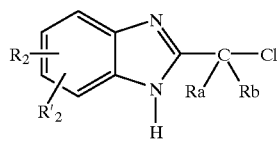

(I/d)

wherein $R_2$, $R'_2$, $R_a$, $R_b$ and X' have the same meanings as hereinabove, which may then be subjected to the conventional reactions that can be carried out on chlorinated compounds, to yield the corresponding substitutions, which compound of formula (I/c) or (I/d):

may, if necessary, be purified in accordance with a conventional purification technique, is separated, where appropriate, into its isomers in accordance with a conventional separation technique, and/or is converted, if desired, into addition salts thereof with a pharmaceutically acceptable acid or base.

The compounds of formula (II), (III) and (IV) are obtained in accordance with conventional methods of the literature adapted to the nature and position of the $R_2$ and $R'_2$ substituents on the phenyl nucleus for compounds of formula (II) or (IV), or $R_a$ and $R_b$ for compounds of formula (III).

The invention relates also to pharmaceutical compositions comprising as active ingredient at least one compound of formula (I) with one or more suitable inert, non-toxic excipents. Amongst the pharmaceutical compositions according to the invention there may be mentioned more especially those which are suitable for oral, parenteral (intravenous or sub-cutaneous) or nasal administration, tablets or dragees, sublingual tablets, gelatin capsules, lozenges, suppositories, creams, ointments, dermal gels, injectable preparations, drinkable suspensions, etc.

The useful dosage can be adapted according to the nature and severity of the affection, the mode of administration and according to the age and weight of the patient, and ranges from 0.1 to 100 mg per day in one or more administrations.

The following Examples illustrate the invention but do not limit it in any way.

The starting materials used are known products or products that are prepared in accordance with known procedures.

The structures of the compounds described in the Examples and in the Preparations have been determined in accordance with the customary spectrophotometric techniques (infrared, NMR, mass spectrometry, etc.).

EXAMPLE 1

2-Phenoximethyl-5-(imidazol-1-yl)benzimidazole dihydrochloride

Step A: 1-(3-Amino-4-nitrophenyl)imidazole 240 mmol of imidazole, 240 mmol of 2-amino4-chloronitrobenzene and 240 mmol of potassium carbonate in 450 ml of dimethylformamide (DMF) are stirred in a 1 litre round-bottomed flask. The mixture is maintained at 130° C. with stirring for 48 hours. After the DMF has been removed by evaporation, the residue is taken up in water. The precipitate that forms is filtered off and then washed with water. It is then dissolved in 550 ml of 1N hydrochloric acid. After insoluble material has been filtered off, the filtrate is rendered alkaline and the precipitate that forms is filtered off and washed with water. After drying, the expected product is obtained after purification by chromatography on silica gel using a dichloromethane/methanol mixture(95/5).

Metting point: 189° C.

Step B: 1-(3,4-Diaminophenyl)imidazole 93 mmol of the compound obtained in the preceding Step are hydrogenated, under atmospheric pressure, in 400 ml of an ethanol/dioxane mixture (50/50) in the presence of 1 g of Pd/C catalyst. After 18 hours' hydrogenation, the mixture is filtered and the filtrate is evaporated to obtain the expected product.

Melting point: 172° C.

Step C: 2-Phenoxymethyl-5-(imidazol-1-yl)benzimidazole dihyd rochloride 34.4 mmol of the product obtained in the preceding Step and 51 mmol of phenoxyacetic acid are refluxed for 18 hours in 120 ml of 4N hydrochloric acid. After cooling, the mixture is rendered alkaline with potassium carbonate. The precipitate that forms is dissolved in methanol. The methanolic solution is decolourised over carbon and then evaporated. The residue is then purified by chromatography on silica gel using a dichloromethane/methanol/ammonium hydroxide mixture (95/5/0.5) as eluant. The purified product is then converted into the corresponding dihydrochloride by dissolution in 1N hydrochloric acid, evaporation and drying.

| Melting point: 186° C. Elemental microanalysis: | | | | |
|---|---|---|---|---|
| | C% | H% | N% | Cl% |
| calculated | 56.21 | 4.44 | 15.42 | 19.52 |
| found | 56.60 | 4.96 | 15.50 | 19.36 |

The products of the following Examples were obtained in accordance with the process described in Example 1, using the corresponding starting materials:

EXAMPLE 2

2-Hydroxymethyl-5-(imidazol-1-yl)benzimidazole dihydrochloride

| Melting point: 235° C. Elemental microanalysis: | | | | |
|---|---|---|---|---|
| | C% | H% | N% | Cl% |
| calculated | 46.01 | 4.21 | 19.51 | 24.69 |
| found | 45.64 | 4.24 | 19.04 | 24.94 |

EXAMPLE 3

2-(4-Methoxyphenoxy)methyl-5-(imidazol-1-yl) benzimidazole dihydrochloride

| Melting point: 190–192° C. (decomp.) Elemental microanalysis: | | | | |
|---|---|---|---|---|
| | C% | H% | N% | Cl% |
| calculated | 54.97 | 4.61 | 14.25 | 18.03 |
| found | 54.66 | 5.10 | 14.02 | 18.03 |

EXAMPLE 4

2-(4-Fluorophenoxy)methyl-5-(imidazol-1-yl) benzimidazole dihydrochloride

| Melting point: 216–218° C. Elemental microanalysis: | | | | |
|---|---|---|---|---|
| | C% | H% | N% | Cl% |
| calculated | 53.56 | 3.97 | 14.70 | 18.60 |
| found | 53.47 | 4.41 | 14.57 | 18.67 |

EXAMPLE 5

2-(2,4-Dichlorophenoxy)methyl-5-(imidazol-1-yl) benzimidazole dihydrochloride

| Melting point: 255–260° C. Elemental microanalysis: | | | | |
|---|---|---|---|---|
| | C% | H% | N% | Cl% |
| calculated | 47.25 | 3.27 | 12.97 | 32.82 |
| found | 46.56 | 3.69 | 12.54 | 32.71 |

EXAMPLE 6

2-(4-Chlorophenoxy)methyl-5-(imidazol-1-yl)benzimidazole dihydrochloride

Melting point: 255° C.
Elemental microanalysis:

|  | C% | H% | N% | Cl% |
|---|---|---|---|---|
| calculated | 51.34 | 3.80 | 14.09 | 26.74 |
| found | 51.91 | 3.74 | 14.05 | 26.23 |

EXAMPLE 7

2-Phenylthiomethyl-5-(imidazol-1-yl)benzimidazole dihydrochloride

Melting point: 189° C.
Elemental microanalysis:

|  | C% | H% | N% | Cl% | S% |
|---|---|---|---|---|---|
| calculated | 53.83 | 4.25 | 14.77 | 18.69 | 8.45 |
| found | 54.07 | 4.23 | 14.60 | 19.19 | 8.36 |

EXAMPLE 8

2-Phenylsulphonylmethyl-5-(imidazol-1-yl)benzimidazole

Elemental microanalysis:

|  | C% | H% | N% | Cl% | S% |
|---|---|---|---|---|---|
| calculated | 49.64 | 3.92 | 13.62 | 17.24 | 7.80 |
| found | 49.95 | 3.83 | 13.38 | 17.62 | 7.76 |

EXAMPLE 9

2-Hydroxymethyl-5-(benzimidazol-1-yl)benzimidazole dihydrochloride

Melting point: >260° C.
Elemental microanalysis:

|  | C% | H% | N% | Cl% |
|---|---|---|---|---|
| calculated | 53.43 | 4.18 | 16.61 | 21.03 |
| found | 53.34 | 3.99 | 16.35 | 21.30 |

EXAMPLE 10

2-Phenoxymethyl-5-(benzimidazol-1-yl)benzimidazole dihydrochloride

Melting point: 210° C. (decomp.)
Elemental microanalysis:

|  | C% | H% | N% | Cl% |
|---|---|---|---|---|
| calculated | 61.03 | 4.39 | 13.56 | 17.16 |
| found | 60.77 | 4.48 | 13.13 | 17.01 |

EXAMPLE 11

2-Phenoxymethyl-5-(4-phenylimidazol-1-yl)benzimidazole

Melting point: 240° C.
Elemental microanalysis:

|  | C% | H% | N% |
|---|---|---|---|
| calculated | 75.39 | 4.95 | 15.29 |
| found | 74.59 | 5.03 | 15.20 |

EXAMPLE 12

2-Hydrocymethyl-5-(4-phenylimidazol-1-yl)benzimidazole dihydrochloride

Melting point: >260° C.
Elemental microanalysis:

|  | C% | H% | N% | Cl% |
|---|---|---|---|---|
| calculated | 56.21 | 4.44 | 15.42 | 19.52 |
| found | 56.21 | 4.37 | 15.44 | 19.35 |

EXAMPLE 13

2-Phenoxymethyl-5-(1,2,4-triazol-4-yl)benzimidazole dihydrochloride

Melting point: 220° C.
Elemental microanalysis:

|  | C% | H% | N% | Cl% |
|---|---|---|---|---|
| calculated | 52.76 | 4.15 | 19.29 | 19.47 |
| found | 52.54 | 4.67 | 19.05 | 21.09 |

EXAMPLE 14

2-Phenoxymethyl-5-(pyrrol-1-yl)benzimidazole

Melting point: 120–122° C.
Elemental microanalysis:

|  | C% | H% | N% |
|---|---|---|---|
| calculated | 74.72 | 5.23 | 14.52 |
| found | 74.65 | 5.52 | 14.02 |

EXAMPLE 15

2-(3-Trifluorophenylthiomethyl)-5-(imidazol-1-yl)benzimidazole

EXAMPLE 16

2-Phenoxymethyl-5-(benzothiazol-2-yl)benzimidazole hydroclloride

Step A : 2-(3,4-Diaminophenyl)benzimidazole

The expected product is obtained in accordance with the process described in Step A of Example 15 starting from 2-(3,4-dinitrophenyl)benzothiazole.

Step B: 2-Phenoxymethyl-5-(benzothiazol-2-yl)benzimidazole hydrochloride

The expected product is obtained in accordance with the process described in Step C of Example 1 starting from the compound obtained in the preceding Step.

Melting point: 222° C.
Elemental microanalysis:

|  | C% | H% | N% | Cl% | S% |
|---|---|---|---|---|---|
| calculated | 64.03 | 4.10 | 10.67 | 9.00 | 8.14 |
| found | 63.60 | 4.19 | 10.56 | 9.43 | 8.06 |

EXAMPLE 17

2-Phenoxymethyl-5-(imidazol[1,2a]pyridin2-yl)benzimidazole

The expected product is obtained in accordance with the process described in Example 16 using the corresponding starting materials.

Elemental microanalysis:

|  | C% | H% | N% |
|---|---|---|---|
| calculated | 74.10 | 4.74 | 16.46 |
| found | 73.92 | 4.69 | 16.27 |

EXAMPLE 18

2-Phenoxymethyl-5-(2-methylthiazol-4-yl)benzimidazole

The expected product is obtained in accordance with the process described in Example 16 using the corresponding starting materials.

Elemental microanalysis:

|  | C% | H% | N% | S% |
|---|---|---|---|---|
| calculated | 67.27 | 4.70 | 13.07 | 9.98 |
| found | 67.64 | 4.62 | 13.01 | 10.16 |

The following Examples were prepared in accordance with the process described in Example 1 using the corresponding starting materials.

EXAMPLE 19

2-Cyclohexyloxymethyl-5-(imidazol-1-yl)benzimidazole

Elemental microanalysis:

|  | C% | H% | N% |
|---|---|---|---|
| calculated | 68.90 | 6.80 | 18.90 |
| found | 69.02 | 6.70 | 18.99 |

EXAMPLE 20

2-Biphenyloxymethyl-5-imidazol-1-yl)benzimidazole dihydrochloride

Elemental microanalysis:

|  | C% | H% | N% | Cl% |
|---|---|---|---|---|
| calculated | 62.88 | 4.59 | 12.75 | 16.14 |
| found | 62.95 | 4.88 | 12.81 | 16.49 |

EXAMPLE 21

2-(3,5-Ditrifluoromethyl)phenoxymethyl-5-(imidazol-1-yl) benzimidazole

Elemental microanalysis:

|  | C% | H% | N% |
|---|---|---|---|
| calculated | 53.53 | 2.84 | 13.14 |
| found | 53.65 | 3.04 | 13.48 |

EXAMPLE 22

2-(3,4-Dimethoxyphenylthiomethyl-5-(imidazol-1-yl)benzimidazole dihydrochloride

| | Elemental microanalysis: | | | | |
|---|---|---|---|---|---|
| | C% | H% | N% | Cl% | S% |
| calculated | 51.94 | 4.59 | 12.75 | 16.14 | 7.30 |
| found | 51.44 | 4.65 | 12.33 | 16.45 | 7.22 |

EXAMPLE 23

2-(4-Methoxyphenylthiomethyl)-5-(imidazol-1-yl)benzimidazole

EXAMPLE 24

2-(3-Trifluoromethylphenoxymethyl)-5-(imidazol-1-yl)benzimidazole dihydrochloride

| | Elemental microanalysis | | | |
|---|---|---|---|---|
| | C% | H% | N% | Cl% |
| calculated | 50.13 | 3.51 | 12.99 | 16.44 |
| found | 50.92 | 3.67 | 13.12 | 15.81 |

EXAMPLE 25

2-(2,6-Dimethylphenoxymethyl)-5-(imidazol-1-yl)benzimidazole dihydrochloride

| | Elemental microanalysis: | | | |
|---|---|---|---|---|
| | C% | H% | N% | Cl% |
| calculated | 58.32 | 5.15 | 14.32 | 18.12 |
| found | 58.30 | 5.27 | 14.09 | 18.23 |

EXAMPLE 26

2-(3,4,5-Trimethoxyphenoxymethyl)-5-(imidazol-1-yl)bezimidazole dihydrochloride

| | Elemental microanalysis: | | | |
|---|---|---|---|---|
| | C% | H% | N% | Cl% |
| calculated | 52.99 | 4.89 | 12.36 | 15.64 |
| found | 53.15 | 5.41 | 12.17 | 14.50 |

EXAMPLE 27

2-(Penylaminomethyl))-5-(imidazol-1-yl)benzimidazole

| | Elemental microanalysis: | | |
|---|---|---|---|
| | C% | H% | N% |
| calculated | 70.57 | 5.23 | 24.20 |
| found | 70.54 | 5.20 | 24.03 |

EXAMPLE 28

2-[(2,6-Di-tert-butyl-4-hydroxy)phenylthionethyl])-5-(imidazol-1-yl)-benzimidazole

EXAMPLE 29

2-(1-(S)-Phenoxyethyl)-5-(imidazol-1-yl)benzimidazole dihydrochloride

| | Elemental microanalysis: | | | |
|---|---|---|---|---|
| | C% | H% | N% | Cl% |
| calculated | 57.31 | 4.81 | 14.85 | 18.79 |
| found | 57.30 | 4.89 | 14.98 | 19.21 |

EXAMPLE 30

2-(1-(R)-Phenoxyethyl)-5-(imidazol-1-yl)benzimidazole dihydrochloride

| | Elemental microanalysis: | | | |
|---|---|---|---|---|
| | C% | H% | N% | Cl% |
| calculated | 57.31 | 4.81 | 14.85 | 18.79 |
| found | 57.31 | 4.84 | 14.82 | 19.09 |

EXAMPLE 31

2-(N-Methylanilinomethyl)-5-(imidazol-1-yl)benzimidazole

| | Elemental microanalysis: | | |
|---|---|---|---|
| | C% | H% | N% |
| calculated | 71.27 | 5.65 | 23.09 |
| found | 70.80 | 5.83 | 22.74 |

EXAMPLE 32

2-(2-Methoxyphenyltiomethyl)-5-(imidazol-1-yl) benzimidazole dihydrochloride

Elemental microanalysis:

|  | C% | H% | N% | Cl% | S% |
|---|---|---|---|---|---|
| calculated | 52.82 | 4.43 | 13.69 | 17.32 | 7.83 |
| found | 52.70 | 4.58 | 13.63 | 17.88 | 8.00 |

EXAMPLE 33

2-(4-Acetamidophenylthiomethyl)-5-(imidazol-1-yl) benzimidazole dihydrochloride

Elemental microanalysis:

|  | C% | H% | N% | Cl% | S% |
|---|---|---|---|---|---|
| calculated | 52.30 | 4.39 | 16.05 | 16.25 | 7.35 |
| found | 51.28 | 4.49 | 15.95 | 16.58 | 7.08 |

EXAMPLE 34

2-(2,6-Dimethylphenylthiomethyl)-5-(imidazol-1-yl) benzimidazole dihydrochloride Elemental microanalysis:

|  | C% | H% | N% | Cl% | S% |
|---|---|---|---|---|---|
| calculated | 56.02 | 4.95 | 13.75 | 17.41 | 7.87 |
| found | 56.32 | 5.08 | 13.66 | 16.92 | 7.78 |

EXAMPLE 35

2-(4-Hydroxyphenylthiomethyl)-5-(imidazol-1-yl) benzimitazole

Elemental microanalysis:

|  | C% | H% | N% | S% |
|---|---|---|---|---|
| calculated | 63.34 | 4.38 | 17.38 | 9.95 |
| found | 63.35 | 4.63 | 17.39 | 9.72 |

EXAMPLE 36

2-(2,6-Dichlorophenoxymethyl)-5-(imidazol-1-yl) benzimidazole dihydrochloride

Elemental microanalysis:

|  | C% | H% | N% | Cl% |
|---|---|---|---|---|
| calculated | 47.25 | 3.27 | 12.97 | 32.82 |
| found | 47.36 | 3.46 | 12.74 | 31.79 |

EXAMPLE 37

2-(2,6-Dimethoxyphenoxymethyl)-5-(imidazol-1-yl) benzimidazole dihydrochloride

Elemental microanalysis:

|  | C% | H% | N% | Cl% |
|---|---|---|---|---|
| calculated | 53.91 | 4.76 | 13.24 | 16.75 |
| found | 54.05 | 4.99 | 13.14 | 16.92 |

EXAMPLE 38

2-(2,6-Diisorpropylphenoxymethyl)-5-(imidazol-1-yl)benzimidazole dihydrochloride Elemental microanalysis:

|  | C% | H% | N% | Cl% |
|---|---|---|---|---|
| calculated | 61.75 | 631 | 12.52 | 15.85 |
| found | 62.45 | 6.47 | 12.55 | 14.99 |

EXAMPLE 39

2-(2,4,6-Trimethylphenoxymethyl)-5-(imidazol-1-yl) benzimidazole dihydrochloride Elemental microanalysis:

|  | C% | H% | N% | Cl% |
|---|---|---|---|---|
| calculated | 59.27 | 5.47 | 13.82 | 17.49 |
| found | 59.36 | 5.82 | 13.78 | 17.23 |

EXAMPLE 40

2-(Cyanomethyl)-5-(imidazol-1-yl)benzimidazole

| | Elemental microanalysis: | | |
|---|---|---|---|
| | C% | H% | N% |
| calculated | 64.56 | 4.06 | 31.37 |
| found | 64.14 | 4.34 | 31.58 |

EXAMPLE 41

2-(1-(S)-Hyroxy-2-phenylethyl)-5-(imidazol-1-yl) benzimidazole dihydrochloride

| | Elemental microanalysis: | | | |
|---|---|---|---|---|
| | C% | H% | N% | Cl% |
| calculated | 57.31 | 4.81 | 14.85 | 18.79 |
| found | 56.84 | 5.52 | 14.55 | 18.76 |

EXAMPLE 42

2-(1-(R)-Hydroxy-2-phenylethyl)-5-(imidazol-1-yl) benzimidazole dihydrochloride

| | Elemental microanalysis: | | | |
|---|---|---|---|---|
| | C% | H% | N% | Cl% |
| calculated | 57.31 | 4.81 | 14.85 | 18.79 |
| found | 56.81 | 5.51 | 14.65 | 18.99 |

EXAMPLE 43

2-(4-Carboxphenoxymethyl)-5-(imidazol-1-yl) benzimidazole

| | Elemental microanalysis: | | |
|---|---|---|---|
| | C% | H% | N% |
| calculated | 64.67 | 422 | 16.76 |
| found | 64.21 | 4.25 | 16.59 |

EXAMPLE 44

2-(2-Ethoxycarbonylphenylthiomethyl)-5-(imidazol-1-yl)benzimidazole

| | Elemental microanalysis: | | | |
|---|---|---|---|---|
| | C% | H% | N% | S% |
| calculated | 63.47 | 4.79 | 14.80 | 8.47 |
| found | 63.87 | 4.94 | 14.70 | 8.31 |

EXAMPLE 45

2{4-(Carboxymethoxy)phenylthiomethyl)-5-(imidazol-1-yl) benzimidazole

| | Elemental microanalysis: | | | |
|---|---|---|---|---|
| | C% | H% | N% | S% |
| calculated | 59.99 | 4.24 | 14.73 | 8.43 |
| found | 60.22 | 4.29 | 14.76 | 8.67 |

EXAMPLE 46

2-(Anilinocarbonylmethyl)-5-imidazol-1-yl) benzimidazole dihydrochloride

| | Elemental microanalysis: | | | |
|---|---|---|---|---|
| | C% | H% | N% | Cl% |
| calculated | 55.40 | 4.39 | 17.94 | 18.17 |
| found | 55.02 | 4.66 | 17.69 | 18.28 |

EXAMPLE 47

2-(Benzoylaminomethyl)-5-(imidazol-1-yl) benzimidazole dihydrochloride

| | Elemental microanalysis: | | | |
|---|---|---|---|---|
| | C% | H% | N% | Cl% |
| calculated | 55.39 | 4.39 | 17.95 | 18.17 |
| found | 55.85 | 4.73 | 18.18 | 17.67 |

EXAMPLE 48

2-(Phenylsulphonylaminomethyl)-5-(imidazol-1-yl) benzimidazole dihydrochloride

Elemental microanalysis:

|  | C% | H% | N% | Cl% | S% |
|---|---|---|---|---|---|
| calculated | 47.90 | 4.02 | 16.43 | 16.63 | 7.52 |
| found | 48.10 | 4.05 | 16.22 | 16.87 | 7.26 |

EXAMPLE 49

2-(Hydroxymethyl)-5-(imidazol-1-yl)-6-(4-fluorophenyl)benzimidazole dihydrochloride Elemental microanalysis:

|  | C% | H% | N% | Cl% |
|---|---|---|---|---|
| calculated | 53.56 | 3.97 | 14.70 | 18.60 |
| found | 53.28 | 3.77 | 14.68 | 19.24 |

EXAMPLE 50

2-(2,6-Dimethoxyphenoxymethyl)-5-(imidazol-1-yl)-6-(4-fluorophenyl)-benzimidazole Elemental microanalysis:

|  | C% | H% | N% |
|---|---|---|---|
| calculated | 67.56 | 4.76 | 12.61 |
| found | 67.34 | 4.98 | 12.63 |

EXAMPLE 51

2-(2,6-Dimethoxyphenoxymethyl)-5-(pyridin-4-yl) benzimidazole

EXAMPLE 52

2-(2,6-Dimethoxyphenoxymethyl)-5-(oxazol-4-yl) benzimidazole

EXAMPLE 53

2-(2,6-Dimethylphenylthiomethyl)-5-(thiazol-4-yl) benzimidazole

EXAMPLE 54

2-(4-Hydroxyaminocarbonylphenoxymethyl)-5-(imidazol-1-yl) benzinidazole

EXAMPLE 55

2-(4-Hydroxyaminocarbonylphenylureidomethyl)-5-(imidazol-1-yl)-benzimidazole

EXAMPLE 56

2-(4-Methylsulphonylaminophenoxymethyl)-5-(imidazol-1-yl) benzimidazole

EXAMPLE 57

2-(Methylsulphonylminocarbonylphenoxyl)-5-(imidazol-1-yl)-benzimidazole

EXAMPLE 58

2-Sulphomethyl-5-(imidazol-1-yl)benzimidazole

EXAMPLE 59

2-(Phenylaminosulphonylmethyl)-5-(imidazol-1-yl) benzimidazole

EXAMPLE 60

2-(Tetrazol-5-yl)methyl-5-imidazol-1-yl) benzimidazole

EXAMPLE 61

2-(3,4-Dicarboxymethoxyphenoxymethyl)-5-(imidazol-1-yl) benzimidazole

EXAMPLE 62

2-(2,4,6-Trimethoxyphenoxymethyl)5-(imidazol-1-yl)benzimidazole

EXAMPLE 63

2-(Pyrrol-2-yloxymethyl)-5-(imidazol-1-yl) benzimidazole

EXAMPLE 64

2-(2,6-Diethoxyphenoxymethyl)-5-(imidazol-1-yl) benzimidazole

EXAMPLE 65

2-(2-Methoxy-6-methylphenoxymethyl)-5-(imidazol-1-yl)benzimidazole

EXAMPLE 66

2-(2,6-Dihydroxyphenoxymethyl)-5-(imidazol-1-yl) benzimidazole

EXAMPLE 67

2-(2-Methoxy-6-hydroxyphenoxymethyl)-5-(imidazol-1-yl) benzimidazole

EXAMPLE 68

2-(2-Hydroxymethyl-6-methoxyphenoxymethyl)-5-(imidazol-1-yl) benzimidazole

EXAMPLE 69

2-(2-Methoxymethyl-6-methoxyphenoxymethyl)-5-(imidazol-1-yl) benzimidazole

EXAMPLE 70

2-(2,6-Dimethoxyphenylthiomethyl)-5-(imidazol-1-yl)benzimidazole

EXAMPLE 71

2-(2,6-Dimethoxyphenylthiomethyl)-5-(imidazol-1-yl)benzimidazole

EXAMPLE 72

2-(2-Methoxy-6-methylphenylthiomethyl)-5-(imidazol-1-yl) benzimidazole

EXAMPLE 73

2-(2,6-Dihydroxyphenylthiomethyl)-5-(imidazol-1-yl)benzimidazole

EXAMPLE 74

2-(2-Methoxy-6-hydroxyphenylthiomethyl)-5-(imidazol-1-yl) benzimidazole

EXAMPLE 75

2-(2,6-Dimethoxyphenylaminomethyl)-5-(imidazol-1-yl)benzimidazole

EXAMPLE 76

2-(2,6-Dimethoxyphenylaminomethyl)-5-(imidazol-1-yl)benzimidazole

EXAMPLE 77

2-(2-Methoxy-6-methylaminomethyl)-5-(imidazol-1-yl)benzimidazole

EXAMPLE 78

2-(2,6-Dihyroxyphenylaminomethyl)-5-(imidazol-1-yl)benzimidazole

EXAMPLE 79

2-(2-Methoxy-6-hydroxyphenylaminoniethyl)-5-(imidazol-1-yl) benzimidazole

EXAMPLE 80

2-[N-(2,6-Dimethoxyphenyl)-N-methylaminomethyl]-5-(iminazol-1-yl) benzimidazole

EXAMPLE 81

2-[N-(2,6-Diethoxyphenyl)-N-methylaminomethyl]-5-(imidazol-1-yl) benzimidazole

EXAMPLE 82

2-[N-(2-Methoxy-6-methylphenyl)-N-methylaniomethyl]-5-(imidazol-1-yl)benzimidazole

EXAMPLE 83

2-[N-(2,6-Dihytlroxyphenyl)-N-menthylaminomethyl]-5-(imidazol-1-yl) benzimidazole

EXAMPLE 84

2-[N-(2-Methoxy-6-hydrooxphenyl )-N-methylaminomethyl]-5-(imidazol-1-yl) benzimidazole

EXAMPLE 85

2-(2,6-Dimethoxyphenylthiomethyl)-5-(imidazol-1-yl)-6-(4-fluorophenyl)benzimidazole

EXAMPLE 86

2-(2,6-Dimethoxyphenylaminomethyl)-5imidazol-1-yl)-6-(4-fluorophenyl)benzimidazole

EXAMPLE 87

2-(2,6-Dimethoxyphenoxymethyl)-5-(imidazol-1-yl)-6-imidazol-1-yl) benzimidazole

EXAMPLE 88

2-(2,6-Dimethoxyphenylthiomethyl)-5-(imidazol-1-yl)-6-(imidazol-1-yl) benzimidazole

EXAMPLE 89

2-(2,6-Dimethoxyphenylaminomethyl)-5-(imidazol-1-yl)-6-(imidazol-1-yl)benzimidazole

EXAMPLE 90

2-(2,6-Dimethoxyphenoxymethyl)-5-(imidazol-1-yl)-6-(4-pyridyl) benzimidazole

EXAMPLE 91

2-(2,6-Dimethoxyphenylthiomethyl)-5-(imidazol-1-yl)-6-(4-pyridyl) benzinidazole

EXAMPLE 92

2-(2,6-Dimethoxyphenylaminomethyl)-5-(imidazol-1-yl)-6-(4-pyridyl) benzimidazole

EXAMPLE 93

2-(2,6-Dimethoxyphenoxymethyl)-5-imidazol-1-yl)-6-(4'-fluorobiphenyl)benzimidazole

EXAMPLE 94

2-(2,6-Dimethoxyphenylthiomethyl)-5-(imidazol-1-yl)-6-(4'-fluorobiphenyl)benzimidazole

EXAMPLE 95

2-(2,6-Dimethoxyphenylaminomethyl)-5-(imidazol-1-yl)-6-(4'-fluorobiphenyl)benzimidazole

EXAMPLE 96

2-(2,6-Dimethoxyphenoxymethyl)-5-(imidazol-1-yl)-6-[4-(4-pyridyl) phenyl]benzirnddazole

EXAMPLE97

2-(2,6-Dimethoxyphenylthiomethyl)-5-imidazol-1-yl)-6-[4-(4-pyridyl) phenyl]benzimidazole

EXAMPLE 98

2-(2,6-Dimethoxyphenylaminomethyl)-5-(imidazol-1-yl)-6-[4-(4-pyridyl)phenyl]benzimidazole

EXAMPLE 99

2-[N-(2,6-Dimethoxyphenythyl)-N-methylaminomethyl]-5-(imidazol-1-yl)-6-(4-fluorophenyl)benzimidazole

EXAMPLE 100

2-[N-(2,6-Dimethoxyphenyl)-N-methylaminomethyl]-5-(imidazol-1-yl)-6-(imidazol-1-yl)benzimidazole

EXAMPLE 101

2-[N-(2,6-Dimethoxyphenyl)-N-methylaminomethyl]-5-(imidazol-1-yl)-6-(4-pyridyl) benzimidazole

EXAMPLE 102

2-[N-(2,6-Dimethoxyphenyl)-N-methylaminomethyl]-5-(imidazol-1-yl)-6-(4'-fluorobiphenyl)benzimidazole

EXAMPLE 103

2-[N-(2,6-Dimethoxyphenyl)-N-methylaminonethyl)]-5-(imidazol-1-yl)-6-[4-(4-pyridyl)phenyl]benzimidazole Pharmacological Study of the Compounds of the Invention

EXAMPLE 104

The compounds were studied on the human monocyte/macrophage type cell line THP1. Production of IL1β by those cells was obtained after stimulation with bacterial lipopolysaccharide (M. Turner et al., *Biochem. Biophys. Res. Comm.*, 1988, 256(2), 830–839) and was determined by the EIA method (Cayman kit) in accordance with the manufacturer's instructions. In the test for endotoxic shock brought about in mice by intravenous injection of lipopolysaccharide, the compounds of the invention reduced the circulating levels of TNF at an oral dose of less than or equal to 100 mg.kg. The $ED_{50}$ were 30, 10, 3 and 10 mg/kg p.o. for the compounds of Examples 48, 34, 37 and 50, respectively.

EXAMPLE 105

Pharmaceutical composition

Formulation for the preparation of 1000 tablets each containing 10 mg of active ingredient

| | |
|---|---|
| Compound of EXAMPLE 1 | 10 g |
| Hydroxypropyl cellulose | 2 g |
| Wheat starch | 10 g |
| Lactose | 100 g |
| Magnesium stearate | 3 g |
| Talc | 3 g |

We claim:
1. A compound selected from those of formula (I):

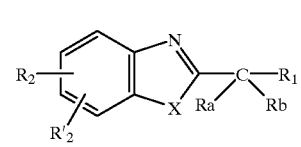

(I)

wherein:

$R_1$ represents hydroxy, linear or branched $(C_1–C_6)$alkoxy (optionally substituted by aryl), trihalomethyl, cyano, sulpho, amino substituted by one or more, identical or different, linear or branched $(C_1–C_6)$alkyl, optionally substituted aryl, acyl, arylsulphonyl and/or alkylsulphonyl), mercapto, linear or branched $(C_1–C_6)$ alkylthio, linear or branched $(C_1–C_6)$ trialkylammonium, aryloxy, arylthio wherein aryl is an aromatic group containing no hetero atoms, arylaminocarbonyl, arylcarbonylamino, arylsulphonylamino, arylaminosulphonyl, arylureido, arylthioureido, arylsulphonyl, arylsulphonyloxy, $(C_3–C_7)$-cycloalkyloxy, $(C_3–C_7)$cycloalkylthio, $(C_6–C_8)$bicycloalkyloxy (optionally substituted by aryl), or $(C_6–C_8)$bicycloalkylthio (optionally substituted by aryl), it being understood that each aryl is optionally substituted, Ra and Rb, which may be identical or different, represent hydrogen, hydroxy, or linear or branched $(C_1–C_6)$alkyl (optionally substituted by aryl), X represents NR (wherein R represents hydrogen or linear or branched $(C_1–C_6)$alkyl), $R_2$ represents imidazolyl, benzimidazol-1-yl, naphthyl, pyridyl, thiazolyl, oxazolyl, benzothiazolyl, benzoxazolyl, pyrrolyl, furyl, thienyl, imidazopyridinyl, triazolyl, or tetrazolyl, each of those groups being optionally substituted by one or more, identical or different, halogen, linear or branched ($C_1$–$C_6$)alkyl, linear or branched ($C_1$–$C_6$)trihaloalkyl, linear or branched ($C_1$–$C_6$)alkoxy, nitro, cyano, carboxy, linear or branched ($C_1$–$C_6$)alkoxycarbonyl, hydroxy, amino (optionally substituted by one or more, identical or different, linear or branched ($C_1$–$C_6$)alkyl, acyl, alkylsulphonyl, and/or arylsulphonyl), optionally-substituted phenyl, and/or optionally-substituted bicycloalkyl, $R'_2$ represents hydrogen or optionally-substituted aryl,
the term "aryl group" being understood to mean a mono- or bi-cyclic aromatic group optionally containing 1 to 4 hetero atoms selected from nitrogen, sulphur, and oxygen, and the term "optionally substituted" as applied to the aryl, phenyl and bicycloalkyl groups meaning a substitution of those groups by one or more, identical or different, halogen atoms, linear or branched ($C_1$–$C_6$)alkyl, linear or branched ($C_1$–$C_6$)trihaloalkyl, linear or branched ($C_1$–$C_6$)alkoxy (optionally substituted by a carboxy or alkoxycarbonyl group), hydroxy, nitro, cyano, amino (optionally substituted by one or more, identical or different, linear or branched ($C_1$–$C_6$)alkyl, acyl, alkylsulphonyl and/or arylsulphonyl groups), carboxy, linear or branched ($C_1$–$C_6$)alkoxycarbonyl, hydroxyaminocarbonyl, alkylsulphonylamino, arylsulfonylamino, alkylsulphonylaminocarbonyl, arylsulphonylaminocarbonyl, optionally substituted phenyl, and/or optionally substituted bicycloalkyl groups,
their isomers and addition salts thereof with a pharmaceutically-acceptable acid or base.

2. A compound of claim 1 wherein $R_1$ represents optionally-substituted aryloxy.

3. A compound of claim 1 wherein $R_1$ represents optionally-substituted arylthio wherein aryl is an aromatic group containing no hetero atoms.

4. A compound of claim 1 wherein $R_1$ represents optionally-substituted arylsulphonylamino.

5. A compound of claim 1 wherein $R_1$ represents optionally-substituted phenoxy.

6. A compound of claim 3 wherein $R_1$ represents optionally-substituted phenylthio.

7. A compound of claim 5 wherein $R_1$ represents optionally-substituted phenylsulphonylamino.

8. A compound of claim 1 wherein $R_2$ represents optionally-substituted imidazolyl.

9. The compound of claim 1 which is 2-phenoxymethyl-5-(imidazol-1-yl)benzimidazole, and addition salts thereof.

10. The compound of claim 1 which is 2-phenylthiomethyl-5-(imidazol-1-yl)benzimidazole, and addition salts thereof.

11. The compound of claim 1 which is 2-(2,6-dimethylphenylthiomethyl)-5-(imidazol-1-yl) benzimidazole dihydrochloride.

12. The compound of claim 1 which is 2-(2,6-dimethoxyphenoxymethyl)-5-(imidazol-1-yl)benzimidazole dihydrochloride.

13. The compound of claim 1 which is 2-(phylsulphonylaminomethyl)-5-(imidazol-1-yl) benzimidazole dihydrochloride.

14. The compound of claim 1 which is 2-(2,6-dimethoxyphenoxymethyl)-5-(imidazol-1-yl)-6-(4-fluorophenyl)benzimidazole.

15. A pharmaceutical composition useful as an interleukin 1β inhibitor of comprising as active principle an effective amount of a compound as claimed in claim 1, together with one or more pharmaceutically-acceptable excipients or vehicles.

16. A method for treating a living body afflicted with a condition requiring an inhibitor of interleukin 1β comprising the step of administering to the living body an amount of a compound selected from those of formula (I):

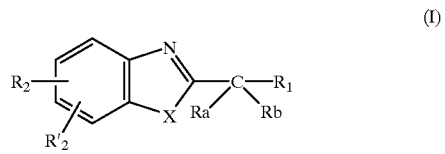

wherein:
$R_1$ represents halogen, hydroxy, linear or branched ($C_1$–$C_6$)alkoxy (optionally substituted by aryl), trihalomethyl, cyano, sulpho, amino (optionally substituted by one or more, identical or different, linear or branched ($C_1C_6$)alkyl, optionally substituted aryl, acyl, arylsulphonyl and/or alkylsulphonyl), mercapto, linear or branched ($C_1$–$C_6$)alkylthio, linear or branched ($C_1$–$C_6$)trialkylammonium, aryloxy, arylthio, arylaminocarbonyl, arylcarbonylamino, arylsulphonylamino, arylaminosulphonyl, arylureido, arylthioureido, arylsulphonyl, arylsulphonyloxy, ($C_3$–$C_7$)-cycloalkyloxy, ($C_3$–$C_7$)cycloalkylthio, ($C_6$–$C_8$)bicycloalkyloxy (optionally substituted by aryl), or ($C_6$–$C_8$)bicycloalkylthio (optionally substituted by aryl), it being understood that each aryl is optionally substituted, Ra and Rb, which may be identical or different, represent hydrogen, hydroxy, or linear or branched ($C_1$–$C_6$)alkyl (optionally substituted by aryl), X represents NR (wherein R represents hydrogen or linear or branched ($C_1$–$C_6$)alkyl), $R_2$ represents imidazolyl, benzimidazol-1-yl, naphthyl, pyridyl, thiazolyl, oxazolyl, benzothiazolyl, benzoxazolyl, pyrrolyl, furyl, thienyl, imidazopyridinyl, triazolyl, or tetrazolyl, each of those groups being optionally substituted by one or more, identical or different, halogen, linear or branched ($C_1$–$C_6$)alkyl, linear or branched ($C_1$–$C_6$)trihaloalkyl, linear or branched ($C_1$–$C_6$)alkoxy, nitro, cyano, carboxy, linear or branched ($C_1$–$C_6$)alkoxycarbonyl, hydroxy, amino (optionally substituted by one or more, identical or different, linear or branched ($C_1$–$C_6$)alkyl, acyl, alkylsulphonyl, and/or arylsulphonyl), optionally-substituted phenyl, and/or optionally-substituted bicycloalkyl, $R'_2$ represents hydrogen or optionally-substituted aryl,
the term "aryl group" being understood to mean a mono- or bi-cyclic aromatic group optionally containing 1 to 4 hetero atoms selected from nitrogen, sulphur, and oxygen, and the term "optionally substituted" as applied to the aryl, phenyl and bicycloalkyl groups meaning a substitution of those groups by one or more, identical or different, halogen atoms, linear or branched ($C_1$–$C_6$)alkyl, linear or branched ($C_1$–$C_6$)trihaloalkyl, linear or branched ($C_1$–$C_6$)alkoxy (optionally substituted by a carboxy or alkoxycarbonyl group), hydroxy, nitro, cyano, amino (optionally substituted by one or more, identical or different, linear or branched $(C_1-C_6)$alkyl, acyl, alkylsulphonyl and/or arylsulphonyl groups), carboxy, linear or branched $(C_1-C_6)$alkoxycarbonyl, hydroxyaminocarbonyl, alkylsulphonylamino, arylsulfonylamino, alkylsulphonylaminocarbonyl, arylsulphonylaminocarbonyl, optionally substituted phenyl, and/or optionally substituted bicycloalkyl groups, their isomers and addition salts thereof with a pharmaceutically-acceptable acid or base, which is effective for the alleviation of said condition.

* * * * *

UNITED STATES PATENT AND TRADEMARK OFFICE
CERTIFICATE OF CORRECTION

PATENT NO.   : 6,040,327
DATED        : March 21, 2000
INVENTOR(S)  : G. De Nanteuil, B. Portevin, J. Bonnet, A. Fradin It is certified that error appears in the above-indentified patent and that said Letters Patent is hereby corrected as shown below:

Cover Page, [56] References Cited, FOREIGN PATENT
    DOCUMENTS, Column 1: The following "names" should
    follow next to each country:
    -- 1450560  8/1966  France  Chimetron
       3819823  12/1989 Germany Ganzer et al.
       2-306916    12/1990 Japan Nishi et al. --.

Cover Page, [56] References Cited, FOREIGN PATENT
    DOCUMENTS, Column 2: The following "NAME" should
    follow next to the country:
    -- 95/19772  7/1995  WIPO  Dykstra et al. --.

Column 1, line 56: "triallylarnmonium group," should
    read -- trialkylammonium group, --.

Column 1, line 58: "arylsulphonylarnino group," should
    read -- arylsulphonylamino group, --.

Column 2, line 7: After the word "group)," begin a new
    sentence <u>inserting</u> the following: -- $R_2$ represents
    an imidazolyl, benzimidazol-1-yl, naphthyl, pyridyl,
    thiazolyl, oxazolyl, benzothiazolyl, benzoxazolyl,
    pyrrolyl, furyl, thienyl, imidazopyridinyl, --.

UNITED STATES PATENT AND TRADEMARK OFFICE
CERTIFICATE OF CORRECTION

PATENT NO. : 6,040,327
DATED : March 21, 2000
INVENTOR(S) : G. De Nanteuil, B. Portevin, J. Bonnet, A. Fradin It is certified that error appears in the above-indentified patent and that said Letters Patent is hereby corrected as shown below:

Column 2, line 67: "formula (I):" should read
    -- formula (II): --.

Column 5, line 19: "2-Phenoximethyl-" should read
    -- 2-Phenoxymethyl- --.

Column 5, line 44: "dihyd rochloride" should read
    -- dihydrochloride --.

Column 6, line 4: "(imidazol-1-yl)" should read
    -- (imidazolyl-1-yl) --.

Column 8, line 38(approx): "2-Hydrocymethyl-" should
    read: -- 2-Hydroxymethyl- --.

Column 9, line 22: At the end of the line,
    "hydrodlloride" should read: -- hydrochloride --.

Column 9, line 23: At the end of the line,
    "benzimidazole" should read: -- benzothiazole --.

Column 12, line 4(aprox.): "2-(Penylaminomethyl)-"
    should read: -- 2-(Phenylaminomethyl)- --.

Column 12, line 19: "phenylthionethyl)-" should read:
    -- phenylthiomethyl)- --.

UNITED STATES PATENT AND TRADEMARK OFFICE
CERTIFICATE OF CORRECTION

PATENT NO. : 6,040,327
DATED : March 21, 2000
INVENTOR(S) : G. De Nanteuil, B. Portevin, J. Bonnet, A. Fradin It is certified that error appears in the above-indentified patent and that said Letters Patent is hereby corrected as shown below:

Column 13, line 5: "2-(2-Methoxyphenyltiomethyl)-" should read -- 2-(2-Methoxyphenylthiomethyl)- --.

Column 13, line 57: "benzimitazole" should read -- benzimidazole --.

Column 15, line 21(approx.): "2-(1-(S)-Hyroxy-" should read -- 2-(1-(S)-Hydroxy- --.

Column 15, line 56: "2-(4-Carboxphenoxymethyl)-" should read -- 2-(4-Carboxyphenoxymethyl)- --.

Column 15, line 64(approx): In the "calculated column" under "H%", "422" should read -- 4.22 --.

Column 16, line 39: "-5-imidazol-1-yl)" should read: -- -5-(imidazol-1-yl) --.

Column 17, line 61: "benzinidazole" should read: -- benzimidazole --.

Column 18, line 9(approx): "2-(Methylsulphonylmino" should read: -- 2-(Methylsulphonylamino --.

Column 18, line 25: "5-imidazol-1-yl)" should read -- 5-(imidazol-1-yl) --.

UNITED STATES PATENT AND TRADEMARK OFFICE
CERTIFICATE OF CORRECTION

PATENT NO. : 6,040,327
DATED : March 21, 2000
INVENTOR(S) : G. De Nanteuil, B. Portevin, J. Bonnet, A. Fradin It is certified that error appears in the above-indentified patent and that said Letters Patent is hereby corrected as shown below:

Column 19, line 59:   "-Dihyroxyphenylaminomethyl)-"
    -- -Dihydroxyphenylaminomethyl)- --.

Column 19, line 65:   "-hydroxyphenylaminoniethyl)" should
    read:   -- 6-hydroxyphenylaminomethyl) --.

Column 20, line 16:   "methylaniomethyl]-" should read:
    -- methylaminomethyl]- --.   Page 23, line 3

Column 20, line 20:   "2-[N-(2,6-Dihytlilroxyphenyl)-"
    should read -- 2-[N-2,6-Dihydroxyphenyl)- --.

Column 20, line 27(approx):   In the middle of the
    formula, "hydrooxphenyl)-" should read:
    -- hydroxyphenyl)- --.

Column 20, line 38(approx):   "-5imidazol-1-" should
    read -- -5-(imidazol-1- --.

Column 20, line 45:   "yl)-6-imidazol-1-yl)" should read:
    -- yl)-6-(imidazol-1-yl) --.

Column 20, line 66:   At the end of the line,
    "benzinidazole" should read:   -- benzimidazole --.

Column 21, line 24:   At the end of the line,
    "benzirnddazole" should read:   --benzimidazole --.

UNITED STATES PATENT AND TRADEMARK OFFICE
CERTIFICATE OF CORRECTION

PATENT NO. : 6,040,327
DATED : March 21, 2000
INVENTOR(S) : G. De Nanteuil, B. Portevin, J. Bonnet, A. Fradin It is certified that error appears in the above-indentified patent and that said Letters Patent is hereby corrected as shown below:

Column 21, line 28(approx): "-5-imidazol-1-" should read: -- -5-(imidazol-1- --.

Column 21, line 39: "-Dimethoxyphenylthyl)-N-" should read -- -Dimethoxyphenyl)-N- --.

Column 21, line 64(approx): "methylaminonethyl)]-" should read -- methylaminomethyl]- --.

Column 23, line 61: "2-phylsulphonylaminomethyl)-" should read -- 2-phenylsulphonylaminomethyl)- --.

Column 23, line 67: The word "of" should be deleted.

Signed and Sealed this

Sixth Day of February, 2001

Attest:

Q. TODD DICKINSON

Attesting Officer

Director of Patents and Trademarks